United States Patent
Dobry et al.

(10) Patent No.: US 8,834,929 B2
(45) Date of Patent: Sep. 16, 2014

(54) DRYING OF DRUG-CONTAINING PARTICLES

(75) Inventors: Daniel Elmont Dobry, Bend, OR (US); Rodney James Ketner, Bend, OR (US); David Keith Lyon, Bend, OR (US); James Mathew Mullin, Bend, OR (US)

(73) Assignee: Bend Research, Inc., Bend, OR (US)

( * ) Notice: Subject to any disclaimer, the term of this patent is extended or adjusted under 35 U.S.C. 154(b) by 725 days.

(21) Appl. No.: 12/309,438

(22) PCT Filed: Jul. 9, 2007

(86) PCT No.: PCT/IB2007/001994
§ 371 (c)(1),
(2), (4) Date: Aug. 31, 2009

(87) PCT Pub. No.: WO2008/012617
PCT Pub. Date: Jan. 31, 2008

(65) Prior Publication Data
US 2010/0028440 A1    Feb. 4, 2010

Related U.S. Application Data

(60) Provisional application No. 60/807,950, filed on Jul. 21, 2006.

(51) Int. Cl.
*A61K 9/14*     (2006.01)
*A61K 9/16*     (2006.01)

(52) U.S. Cl.
CPC .................................. *A61K 9/1694* (2013.01)
USPC ......................................................... 424/489

(58) Field of Classification Search
None
See application file for complete search history.

(56) References Cited

U.S. PATENT DOCUMENTS

| | | | |
|---|---|---|---|
| 3,889,388 A | 6/1975 | Oguri et al. | |
| 4,170,074 A | 10/1979 | Heckman et al. | |
| 6,572,893 B2 * | 6/2003 | Gordon et al. ................. | 424/489 |
| 2003/0037459 A1 | 2/2003 | Chickering et al. | |
| 2003/0198674 A1 | 10/2003 | Curatolo et al. | |
| 2003/0215515 A1 | 11/2003 | Truong-Le et al. | |
| 2008/0213375 A1 | 9/2008 | Ray et al. | |

FOREIGN PATENT DOCUMENTS

| | | |
|---|---|---|
| CA | 2560984 | 12/2005 |
| EP | 1027887 | 8/2000 |
| WO | WO03/063821 | 8/2003 |
| WO | 2004/014342 A1 | 2/2004 |
| WO | 2005/053651 A1 | 6/2005 |

OTHER PUBLICATIONS

GEA Process Engineering, Basics of Spray Drying, http://www.niroinc.com/technologies/basics_of_spray_drying.asp, last accessed: Dec. 15, 2011, pp. 1-3.*
Jones, David M., "Fluidized Bed Processing and Drying," Pharmaceutical Engineering, 8 pages (Mar. 1991).
International Search Report for PCT/IB2006/000186 (Sep. 1, 2006).

* cited by examiner

*Primary Examiner* — Trevor Love
(74) *Attorney, Agent, or Firm* — Klarquist Sparkman, LLP

(57) ABSTRACT

A secondary drying process is disclosed for removing residual solvent from drug-containing particles that have been formed by solvent-based processes.

11 Claims, 4 Drawing Sheets

DRYING OF DRUG-CONTAINING PARTICLES

This is a 371 of PCT/IB/2007/001994 filed 9 Jul. 2007, and claims priority of U.S. 60/807,950 filed 21 Jul. 2006.

BACKGROUND OF THE INVENTION

Processes that utilize a liquid or solvent are routinely used in the preparation of solid pharmaceutical compositions. Recently it has been discovered that some pharmaceutical compositions made by a spray-drying process can enhance the aqueous concentration and bioavailability of low-solubility drugs. See, for example, commonly owned EP 0 901 786 A2, which discloses forming solid amorphous dispersions of low-solubility drugs and the cellulosic polymer hydroxypropyl methyl cellulose acetate succinate (HPMCAS) by spray-drying, and commonly owned WO 03/000238 A1, which discloses forming adsorbates of a low-solubility drug onto high surface area substrates using a spray-drying process. Such dispersions and adsorbates contain non-crystalline drug in the form of drug-containing particles, and exhibit concentration enhancement of the drug relative to crystalline drug alone.

Pharmaceutical compositions made by solvent processing often contain a low concentration of the solvent used to form the composition immediately after removal from the apparatus in which they are made. This "residual solvent" may be at a concentration of about 2 to 10 wt %. Since a desirable final residual solvent content in such drug-containing particles is on the order of 1 wt % or less for purposes of drug stability and purity, secondary drying following spray drying is often required. Another characteristic of such particles formed by spray drying is that they tend to be small (less than 500 µm in diameter) and have low density (bulk specific volumes greater than about 1.5 mL/g).

Various dryers have been suggested for removing residual solvent from pharmaceutical compositions, including tray dryers, fluidized-bed dryers, microwave dryers, belt dryers, and rotary dryers. These dryers typically contact the pharmaceutical composition with warm or hot air or an inert gas. However, while such dryers can be effective and are commercially available, all have drawbacks. For example, tray dryers require a substantial amount of time to reduce the solvent content to acceptable levels and are prone to producing non-uniform dried product. Rotary dryers, which consist of a rotating drying chamber, are typically used for drying small amounts of material and require a substantial amount of time to remove the residual solvent to an acceptable level.

Thus, there is a need in the art for a relatively quick and energy-efficient secondary drying process for producing drug-containing particles with acceptable residual solvent content.

BRIEF SUMMARY OF THE INVENTION

In one aspect, the invention provides a process for producing a pharmaceutical composition, the process comprising: (a) spraying a mixture comprising a drug, an excipient and a solvent to form at least partially non-crystalline drug-containing particles, wherein the drug-containing particles contain less than about 10 wt % of the solvent; and (b) drying the drug-containing particles by (i) exposing the particles in a chamber to a volatile mobility-enhancing agent that is different from the solvent, so that the glass-transition temperature of the particles is reduced relative to control particles free of the solvent and the volatile mobility-enhancing agent; (ii) introducing a stripping gas into the chamber; and (iii) removing the stripping gas from the chamber along with at least a portion of the solvent.

In another aspect, the invention provides a process for producing a pharmaceutical composition, the process comprising: (a) spraying a mixture comprising a drug, an excipient and a solvent to form at least partially non-crystalline drug-containing particles, wherein the drug-containing particles contain less than about 10 wt % of the solvent; and (b) drying the drug-containing particles by (i) exposing the particles in a chamber to a volatile mobility-enhancing agent that is different from the solvent, the volatile mobility-enhancing agent being selected from the group consisting of water, ethanol, isopropyl alcohol, carbon dioxide, and mixtures thereof, and the volatile mobility-enhancing agent being present in the chamber at a partial pressure of at least 0.02 atm; (ii) introducing a stripping gas into the chamber; and (iii) removing the stripping gas from the chamber along with at least a portion of the solvent.

In yet another aspect, the invention provides a process for producing a pharmaceutical composition, the process comprising: (a) spraying a mixture comprising a drug, an excipient and a solvent to form at least partially non-crystalline drug-containing particles, wherein the drug-containing particles contain less than about 10 wt % of the solvent; and (b) drying the drug-containing particles by (i) exposing the particles in a chamber to a volatile mobility-enhancing agent that is different from the solvent, the volatile mobility-enhancing agent being selected from the group consisting of water, ethanol, and mixtures thereof, and the volatile mobility-enhancing agent being present in the chamber at a partial pressure of at least 0.02 atm; (ii) introducing a stripping gas into the chamber; and (iii) removing the stripping gas from the chamber along with at least a portion of the solvent.

In still another aspect, the invention provides a process for producing a pharmaceutical composition, the process comprising: (a) spraying a mixture comprising a drug, an excipient and a solvent to form at least partially non-crystalline drug-containing particles, wherein the drug-containing particles contain less than about 10 wt % of the solvent; and (b) drying the drug-containing particles by (i) exposing the particles in a chamber to water so that the relative humidity in the chamber is at least about 30%; (ii) introducing a stripping gas into the chamber; and (iii) removing the stripping gas from the chamber along with at least a portion of the solvent.

In another aspect, the invention provides a process for producing a pharmaceutical composition, the process comprising: (a) spraying a mixture comprising a drug, an excipient and a solvent to form at least partially non-crystalline drug-containing particles, wherein the drug-containing particles contain less than about 10 wt % of the solvent; and (b) drying the drug-containing particles by (i) evaporating a volatile mobility-enhancing agent in liquid form into a carrier gas to form a vapor-containing gas; (ii) contacting the particles in a chamber with the vapor-containing gas; (iii) introducing a stripping gas into the chamber; and (iv) removing the stripping gas from the chamber along with at least a portion of the solvent.

In another aspect, the invention provides a process for producing a pharmaceutical composition, the process comprising: (a) spraying a mixture comprising a drug, a polymer, and a solvent to form particles comprising a solid amorphous dispersion of the drug in the polymer, the solid amorphous dispersion particles containing less than 10 wt % of the solvent; and (b) drying the drug-containing particles by (i) evaporating a volatile mobility-enhancing agent in liquid form into a carrier gas to form a vapor-containing gas; (ii)

contacting the particles in a chamber with the vapor-containing gas; (iii) introducing a stripping gas into the chamber; and (iv) removing the stripping gas from the chamber along with at least a portion of the solvent.

In still another aspect, the invention provides a process for producing a pharmaceutical composition, the process comprising: (a) spraying a mixture comprising a drug, a polymer, and a solvent to form particles comprising a solid amorphous dispersion of the drug in the polymer, the solid-amorphous dispersion particles containing less than about 10 wt % of the solvent; and (b) drying the drug-containing particles by (I) evaporating water into a carrier gas to form a water-vapor-containing gas; (ii) contacting the particles in a chamber with the water vapor-containing gas so that the relative humidity in the chamber is at least 30%; (iii) introducing a stripping gas into the chamber; and (iv) removing the stripping gas from the chamber along with at least a portion of the solvent.

Pharmaceutical compositions made by solvent processing typically are in the form of small particles. Each of these small particles contains residual solvent that must be removed to acceptable levels. The rate at which residual solvent is removed from such particles will depend on several factors. The rate at which heat is transferred into the particles must be sufficiently rapid to overcome evaporative cooling so as to maintain a high enough particle temperature such that evaporation of the solvent from the particle is rapid. A high driving force for evaporation of the residual solvent must be maintained to ensure rapid evaporation of solvent from the particle (e.g., to maintain high mass-transfer rates). Conventional wisdom dictates that to ensure good mass-transfer residual solvent removal should be conducted in as dry an environment as possible.

The problem with drying particles of amorphous material using conventional processes is that it becomes progressively more difficult to remove solvent from the particles. For example, the time required to reduce the residual solvent content from 3 wt % to 1 wt % may take about 1 hour, while the time required to reduce the residual solvent content from 1 wt % to 0.5 wt % may take 6 hours. Thus, long periods of time may be required to achieve low residual solvent levels.

The inventors believe that when at least a portion of the pharmaceutical composition is non-crystalline, the rate at which the residual solvent can diffuse from the interior of the particle to the outside is also critical in determining the rate at which residual solvent is removed. The inventors have found that as more of the residual solvent is removed from the particles, the rate at which the solvent is removed from the particle decreases. Without wishing to be bound by any particular theory, the inventors believe that an increase in the glass transition temperature ($T_g$) of the particles is a significant factor in the reduced rate of residual solvent removal. Specifically, as solvent is removed from the non-crystalline particles, the $T_g$ of the particles increases. This slows the rate at which solvent can diffuse from the interior to the surface of the particles.

The inventors solved the problem of long drying times by exposing the particles to a volatile mobility-enhancing agent. Surprisingly, the inventors discovered that high rates of solvent removal and high mass-transfer rates can be achieved by exposing the solvent-containing particles to water, ethanol, or similar volatile mobility-enhancing agents that speed the drying process. Without wishing to be bound by any theory or mechanism of action, the inventors believe that when a pharmaceutical composition containing non-crystalline material is exposed to a volatile mobility-enhancing agent, the glass-transition temperature (Tg) of the particles being dried is reduced. This reduced Tg results in an increase in the diffusion rate of the residual solvent present in the particles. Under such conditions, the Tg of the particles remains low due to the presence of the volatile mobility-enhancing agent in the particles, even as the residual solvent is removed. As a result, mass transfer of solvent out of the particles is increased, resulting in faster drying rates than when no volatile mobility-enhancing agent is used.

The secondary drying process of the present invention facilitates mass transfer of the solvent, allowing the solvent to be removed from the drug-containing particles relatively quickly and efficiently. This secondary drying process can also be utilized in a wide range of secondary drying equipment; an existing secondary dryer can be operated according to the process of the present invention by introducing the volatile mobility-enhancing agent into the drug-containing particles, into the drying chamber, into the stripping gas circulated through the equipment, or any combination or all of these methods.

The foregoing and other objectives, features, and advantages of the invention will be more readily understood upon consideration of the following detailed description of the invention.

DETAILED DESCRIPTION OF PREFERRED EMBODIMENTS

Figure 1:
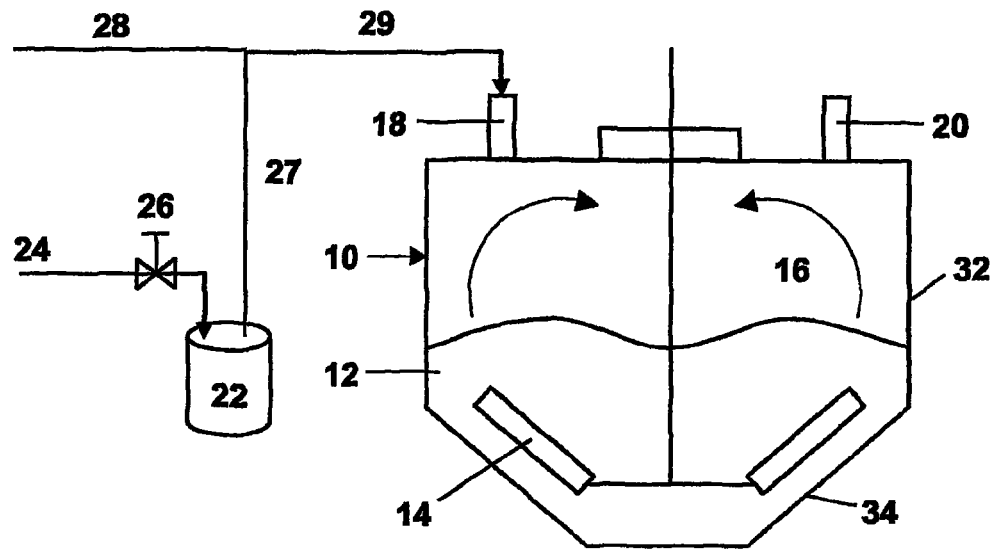
FIG. 1 is a cross-sectional schematic of an exemplary secondary drying apparatus suitable for use in the process of the invention.

The term "about" as used in the specification and claims means the specified value±10% of that value.

Pharmaceutical compositions made by solvent processing typically contain low levels of solvent, referred to herein as "residual solvent." A large fraction of this residual solvent must typically be removed prior to the formation of dosage forms suitable for administration to a patient. The process used to remove this residual solvent is referred to herein as a "secondary drying" process.

Secondary drying processes for drying the pharmaceutical compositions, suitable drugs and compositions are described in detail below.

Secondary Drying Process

A key feature of the secondary drying process of the present invention is the use of a volatile mobility-enhancing agent to improve the rate of residual solvent removal from particles made via solvent-based processes. The volatile mobility-enhancing agent reduces the Tg of the particles, resulting in an increase in the diffusion rate of residual solvent present in the particles.

The volatile mobility-enhancing agent is different from the residual solvent, and can be any material that is pharmaceutically acceptable and that, when exposed to the residual-solvent containing particles, decreases the Tg sufficiently to improve the rate at which residual solvent is removed from the particles. In addition, the volatile mobility-enhancing agent should be volatile, having a boiling point of less than about 150° C., preferably less than 130° C., and more preferably less than about 120° C. Generally, the volatile mobility-enhancing agent is not as good a solvent for the particles to be dried as the solvent used to form the particles. Preferably, the volatile mobility-enhancing agent is more acceptable or has a lower toxicity than the residual solvent present in the particles to be dried. Exemplary volatile mobility-enhancing agents include water, ethanol, isopropyl alcohol, carbon dioxide, and mixtures thereof. Preferred volatile mobility-enhancing agents include water and ethanol. Preferably, the volatile mobility-enhancing agent is water. In one embodiment, the volatile mobility-enhancing agent has a volatility that is less than the volatility of the residual solvent.

The amount of volatile mobility-enhancing agent utilized in the process of the present invention will depend on the nature of the particles containing the residual solvent and the volatile mobility-enhancing agent, but generally should be an amount sufficient such that the Tg of the particles when exposed to the volatile mobility-enhancing agent is at least about 5° C. lower than the Tg of control particles that are free of the residual solvent and the volatile mobility-enhancing agent. By "free of" is meant that essentially all of the residual solvent and volatile mobility-enhancing agent have been removed from the particles. In other words, a sufficient amount of volatile mobility-enhancing agent should be used so that the Tg of the particles when exposed to the volatile mobility-enhancing agent is at least about 5° C. lower than the Tg of completely dry particles (that is, particles that contain essentially no residual solvent and no volatile mobility-enhancing agent). If a material has more than one Tg, a sufficient amount of volatile mobility-enhancing agent is used such that at least one Tg is about 5° C. lower than the corresponding Tg of control particles free of the residual solvent and the volatile mobility-enhancing agent.

Preferably, a sufficient amount of volatile mobility-enhancing agent is used such that the Tg is at least about 10° C., and more preferably, at least about 15° C. lower than the Tg of control particles free of the residual solvent and the volatile mobility-enhancing agent. The Tg of a material, both before and after addition of the volatile mobility-enhancing agent, can be measured by several techniques, including by a dynamic mechanical analyzer (DMA), a dilatometer, a dielectric analyzer, and by differential scanning calorimetry (DSC). Since each of these techniques will give a somewhat different value for the Tg, it is preferred that the same technique be used to determine the Tg of a material before and after addition of the volatile mobility-enhancing agent, and the Tg of the control particles free of the volatile mobility-enhancing agent and residual solvent. Preferably, the Tg is measured by DSC analysis.

The amount of volatile mobility-enhancing agent utilized in the process of the present invention may also be determined by the amount of volatile mobility-enhancing agent absorbed by the material to be dried. Preferably, the material absorbs at least about 0.1 wt % volatile mobility-enhancing agent (mass of agent divided by total mass of material and agent). The inventors have found that the Tg of a material that absorbs this amount of volatile mobility-enhancing agent generally will be about 5° lower than the Tg of the material that is essentially free from residual solvent and the volatile mobility-enhancing agent. More preferably, the material absorbs at least about 0.5 wt %, most preferably at least 1 wt % of the volatile mobility-enhancing agent. The amount of volatile mobility-enhancing agent absorbed by a material may be measured by methods known in the art, preferably by dynamic vapor sorption (DVS).

The absolute amount of volatile mobility-enhancing agent utilized in the process of the present invention will depend on (1) the volatile mobility-enhancing agent used, (2) the composition of the particles to be dried, and (3) the temperature and pressure in the drying chamber. Generally, the partial pressure of volatile mobility-enhancing agent present in the drying chamber should be at least about 0.02 atm, more preferably at least about 0.03 atm, even more preferably at least about 0.04 atm, and most preferably at least about 0.05 atm.

However, if too much volatile mobility-enhancing agent is used, the Tg of the particles may be reduced to a value below the temperature at which the particles are being dried, potentially resulting in undesirable changes to the particle. Therefore, it is also preferred that the Tg of the particles after exposure to the volatile mobility-enhancing agent be greater than the temperature at which the particles are being dried. For example, if the particles are being dried at a temperature of 30° C., the Tg of the particles after exposure to the volatile mobility-enhancing agent is preferably greater than 30° C. Thus, the Tg of the particles after exposure to the volatile mobility-enhancing agent may be greater than about 30° C., may be greater than about 35° C., or may be greater than about 40° C.

The residual-solvent-containing particles can be exposed to the volatile mobility-enhancing agent using any method that allows the volatile mobility-enhancing agent to reduce the Tg of the particles. Exemplary methods for exposing the particles to the volatile mobility-enhancing agent include (1) spraying the volatile mobility-enhancing agent in liquid form onto the particles; (2) mixing the volatile mobility-enhancing agent in solid form with the particles; (3) evaporating the volatile mobility-enhancing agent in liquid form into a carrier gas to form a vapor and contacting the particles with the vapor-containing carrier gas; and (4) any combination or all of (1), (2), and (3). Generally, to facilitate ease of processing, methods (1) and (3) are preferred. In one embodiment, the residual-solvent-containing particles are exposed to the volatile mobility-enhancing agent using method (3). In another embodiment, the carrier gas used in method (3) is the same as the stripping gas. In still another embodiment, the stripping gas is the volatile mobility-enhancing agent in vapor or gas form. In yet another embodiment, the stripping gas and carrier gas, are both the same as the volatile mobility-enhancing agent.

In one embodiment, the volatile mobility-enhancing agent is water that is either sprayed onto the residual-solvent-containing particles or the residual-solvent-containing particles are exposed to an environment containing elevated levels of relative humidity (RH). As used herein, the term "relative humidity" is used in its traditional sense, indicating the ratio of the amount of water vapor in the environment (e.g., the air or atmosphere in contact with the particles) at a specific temperature to the maximum amount of water vapor that the environment could hold at that temperature, expressed as a percentage. Typically, depending on the formulation, the RH of the atmosphere should be at least about 25%, preferably at least about 30 wt %, more preferably at least about 50% RH, and even more preferably at least about 70%. Such RH values generally are sufficient to decrease the Tg of the particles by at least about 5° C., resulting in improved rates of drying.

A stripping gas is used to aid in removal of residual solvent from the particles. The stripping gas can generally be any gas, but is typically selected from air, nitrogen, argon, helium, and carbon dioxide. The volatile mobility-enhancing agent may be present in the stripping gas, the stripping gas acting as a carrier for the volatile mobility-enhancing agent. When carbon dioxide is used, it can serve as both the stripping gas and as the volatile mobility-enhancing agent. The stripping gas may also be the volatile mobility-enhancing agent in vapor or gas form. For example, if water is used as the volatile mobility-enhancing agent, the pressure inside the drying chamber may be reduced and water vapor may be introduced into the drying chamber as both volatile mobility-enhancing agent and as stripping gas. When operating in this mode, it is generally preferred that the temperature and pressure inside the drying chamber be selected such that water vapor does not condense onto the particles being dried. Preferably, the stripping gas is an inert gas such as nitrogen, argon, or helium.

Preferably, the stripping gas entering the drying chamber has a low amount of residual solvent. The lower the concentration of residual solvent in the stripping gas, the higher the driving force for removal of residual solvent from the particles. Generally, the partial pressure of residual solvent in the stripping gas is lower than the equilibrium partial pressure of residual solvent in the particle at any given time for mass transfer to take place. Preferably the partial pressure of residual solvent in the stripping gas is less than 90% relative to the partial pressure of the residual solvent in equilibrium with the particles at the target residual solvent content, and more preferably less than 80%. For example, if the target residual solvent content for the particle is 1 wt %, and the partial pressure of the residual solvent in equilibrium with the particle having a solvent content of 1 wt % is 0.002 atm, then the stripping gas should have a partial pressure of residual solvent that is less than 90% of 0.002 atm; that is, the stripping gas should have a partial pressure of residual solvent of less than 0.0018 atm.

Low partial pressures of residual solvent in the stripping gas may be obtained by (1) using a stripping gas that is essentially free from the residual solvent; (2) treating the stripping gas to remove any residual solvent present prior to introduction into the drying chamber, (3) reducing the total pressure in the drying chamber, and (4) by a combination of (1) and (3) or (2) and (3). Generally, the partial pressure of residual solvent in the stripping gas should be as low as practical to ensure a high driving force for removal of the residual solvent from the particles. Exemplary methods for treating the stripping gas to remove residual solvent include condensers, absorbers, scrubbers, and other processes well know to those skilled in the art.

The total pressure in the drying chamber may also be reduced to reduce the partial pressure of residual solvent in the stripping gas in contact with the particles, thereby increasing the driving force for solvent removal. The pressure within the drying chamber may be less than about 0.75 atm, less than about 0.5 atm, or even less than about 0.1 atm. In general it may be stated that the lower the total pressure is in the drying chamber, the greater is the driving force for removal of solvent from the particles. However, extremely low pressures in the drying chamber require large energy-consuming vacuum pumps. Accordingly, operation at pressures of less than about 0.01 atm is generally not energy-efficient.

Figure 2:
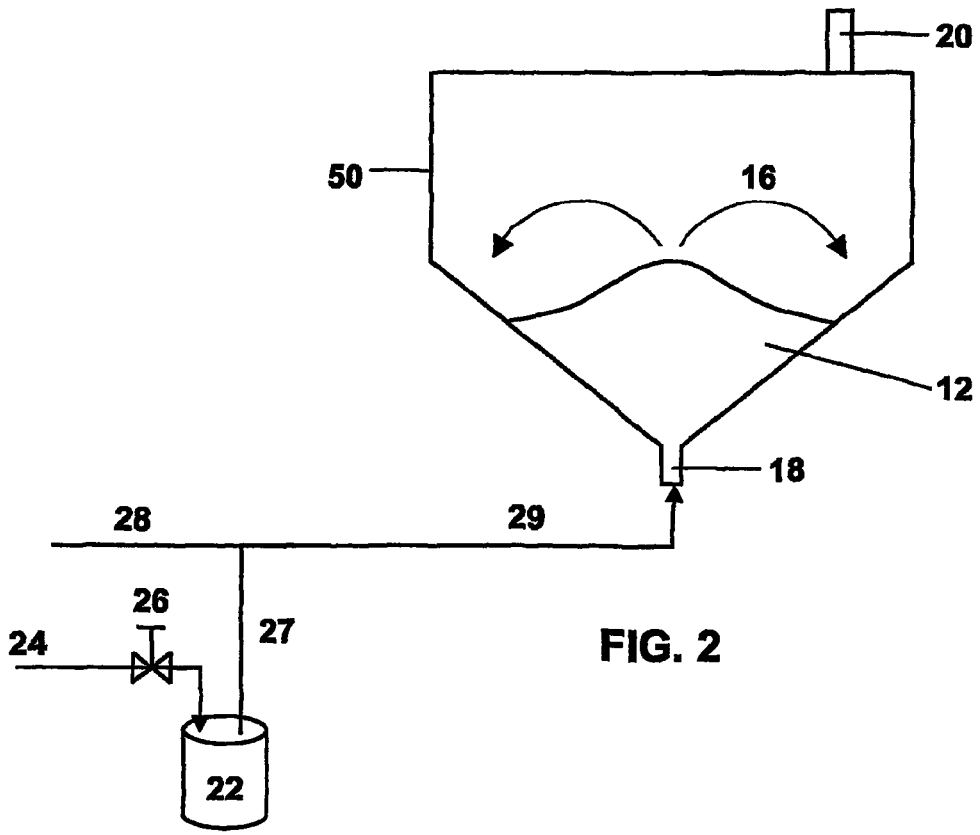
FIG. 2 is a cross-sectional schematic of an alternative exemplary secondary drying apparatus suitable for use in the process of the invention.

FIG. 1 shows schematically in cross section a drying chamber 10 having an upper cylindrical portion 32 connected to a lower conical portion 34, the cone angle ranging from about 60° to about 120°. The drying chamber contains particles 12 and a rotating stir paddle 14 to circulate the particles within the drying chamber into contact with the head space 16. The dying chamber 10 is provided with means for introducing a volatile mobility-enhancing agent into the atmosphere therein. An exemplary means comprises an evaporator 22 that is supplied with volatile mobility-enhancing agent via supply line 24 and throttle valve 26. The vaporized volatile mobility-enhancing agent 27 produced by the evaporator 22 is then mixed with a stripping gas 28 to form a volatile mobility-enhancing agent laden stripping gas 29 that introduces precise amounts of volatile mobility-enhancing agent to the drying chamber. The volatile mobility-enhancing agent laden stripping gas 29 enters the drying chamber 10 through inlet port 18 and exits through outlet port 20, which is connected to a vacuum pump (not shown) to remove stripping gas and solvent. The particles may be agitated with sufficient energy that (1) the particles are flung into the head space; (2) there is frequent contact of the particles with the head space by providing a rapid renewal of particles at the interface with the head space; or (3) a combination of (1) and (2). For example, the arrows in FIG. 1 show the particles being flung into the head space as a result of rapid rotation of the stir paddles. In a preferred embodiment, the mechanical agitation results in good contact of the particles with both the volatile mobility-enhancing agent laden stripping gas and the head space.

For example, FIG. 2 shows an alternative drying chamber 50 in which the inlet port 18 is located at the bottom of the chamber to cause the particles to circulate up into contact with the head space 16. Since the particles are typically very small and have low-density, it is also desired to minimize entrainment of the particles in the stripping gas. This may be accomplished through a variety of techniques. For example, in one embodiment, the total pressure within the drying apparatus may be kept low. This allows the volume of stripping gas to be reduced while still having rapid drying. This reduces entrainment of the particles.

As yet another alternative, the particles may be circulated using a combination of the volatile mobility-enhancing agent laden stripping gas flow and mechanical agitation.

The secondary drying process may also be performed at elevated temperatures to increase the vapor pressure of the solvent and, in turn the driving force for removal of solvent from the particles. This may be accomplished by heating the drying chamber or by heating the stripping gas introduced into the drying chamber, or both. The drying chamber may be heated, for example, by circulating a heating fluid in a jacket surrounding the dryer. Preferably, the drying chamber is at a temperature of at least about 30° C. (that is, the temperature of the heating fluid used to heat the drying chamber is at least about 30° C.). Higher drying temperatures may also be used to increase the rate at which residual solvent is removed from the particles. Thus, the drying chamber may be at a temperature of at least about 35° C., at least about 40° C., at least about 45° C., at least about 50° C., at least about 55° C., or even at least about 60° C.

At least a portion of the solvent in the particles is removed from the drying chamber during the secondary drying process of the invention. By "at least a portion" means that upon completion of the secondary drying process of the invention, the amount of solvent removed from the particles is at least about 50 wt % as compared to the amount of solvent in the particles upon commencement of the secondary drying process, preferably at least about 80 wt %, more preferably at least about 90 wt % and most preferably at least about 95 wt %. In absolute terms, the amount of solvent remaining in the particles is preferably less than about 1 wt % of the total mass of the particles, more preferably less than about 0.5 wt %, and most preferably less than about 0.1 wt %.

The drying process may be conducted in virtually any device or system designed to remove volatile materials from solid particles. Drying equipment which may be utilized with the process of the invention includes a tray dryer, a Turbo tray dryer, a fluid bed dryer, a microwave dryer, a belt dryer, a rotary dryer, a multi-louvre dryer, a rotoevaporator dryer, a vacuum dryer, and an agitated bed vacuum dryer. However, the inventive drying process is especially suitable for devices capable of (1) exposing the particles to a drying environment of low partial pressure of the solvent and high concentration of the volatile mobility-enhancing agent, as previously described, and (2) circulating the particles within the dryer so as to repeatedly move the particles to a position near the upper surface of the particle bed near the head space of the drying chamber. For example, the drying chamber may be similar to the configuration shown in FIGS. 1-2. In one embodiment, the drying chamber is a tray dryer configured such that the volatile mobility-enhancing agent is introduced into the stripping gas that is circulated through the dryer. Alternatively, the volatile mobility-enhancing agent may be sprayed onto the particles before placing in the drying chamber, or while the particles are in the drying chamber. Tray dryers may be equipped with devices to stir or circulate the particles within the dryer. Examples include a tray containing stir paddles, a rotating drum with baffles, or a series of horizontal plates and a rotating shaft with arms and plows that convey the particles from one plate to another. As yet another example, the dryer may be a Turbo tray dryer consisting of a stack of rotating trays, wherein the material is wiped from one tray to the one below. See Perry's *Chemical Engineer's Handbook* Page 20-47 (5$^{th}$ ed. 1973). As another example, the dryer may be a multi-louvre dryer which uses a louvered conveyor which picks up material and dumps it in a thin stream over a ventilated ascending louver. Ibid., page 20-53. Preferably, the drying chamber is made of stainless steel and does not rotate or move during operation of the dryer.

The particles to be dried are typically small and have a low density. Therefore, the drying chamber may be equipped with pneumatic transfer tubes for pneumatically transferring both the particles to be dried and the dried particles into and out of, respectively, the drying chamber. Such pneumatic transfer may be utilized to reduce or eliminate exposure of workers to the particles and to the residual solvent. Pneumatic transfer may also be used to reduce contact of the drug in the drug-containing particles with air, thereby preventing possible oxidation and/or degradation of the drug.

The particles may also be transported into and out of the drying chamber using gravity. In such cases the drying chamber and transfer tubes may be equipped with suitable vibration or hammering devices to ensure adequate flow of the particles from one point to another.

The process of the present invention may be utilized in a batch process or in a continuous process. The particles are typically dried in a batch process by charging the drying chamber with the particles to be dried via either the stripping gas inlet port or another port. The volatile mobility-enhancing agent laden stripping gas may be introduced near the bottom of the drying chamber, near the middle or even in the headspace. Once dried, the drug-containing particles may be discharged via an outlet, such as a port located at the bottom of the drying chamber. The stripping gas outlet port may be provided with a back-pulse filter in fluid communication with a vacuum pump. The particles may also be dried in a continuous process using equipment and procedures well known in the art. One advantage of the process of the present invention is that the rate at which residual solvent is removed from the material is increased over prior art processes, making continuous processes practical.

Solvent-Based Processes

The secondary drying process of the invention is suitable for removing residual solvent from drug-containing particles formed by solvent-based processes wherein at least a portion of the drug-containing particles is in a non-crystalline state.

The term "crystalline" refers to solid material in which atoms or molecules are arranged in a definite pattern that is repeated regularly in three dimensions. The term "non-crystalline" therefore refers to solid material that does not have repeated three-dimensional order. Material in a non-crystalline state is sometimes referred to in the art as being in an amorphous state. "Non-crystalline" is intended to include not only material which has essentially no order, but also material which may have some small degree of order, but the order is in less than in three dimensions and/or is only over short distances. Non-crystalline material may be characterized by techniques known in the art such as powder x-ray diffraction (PXRD), solid state NMR, or thermal techniques such as differential scanning calorimetry (DSC). For example, when evaluated by PXRD, non-crystalline material exhibits a deviation from a flat baseline, referred to in the art as an "amorphous halo." In another example, when evaluated by DSC, non-crystalline material will exhibit a glass transition temperature ($T_g$).

The phrase "at least a portion" in reference to degree of crystallinity means that at least about 10 wt % of the material in the particles is in a non-crystalline or an amorphous state. The process of the invention finds greater utility as the percentage of the noncrystalline material in the particles increases. Thus, the amount of non-crystalline material present in the particles may be at least about 25 wt %, at least about 50 wt %, at least about 75 wt %, or even at least about 95 wt %. In one embodiment, essentially all of the material in the particles is non-crystalline, meaning that essentially no crystalline material is present in the particles within the detection limits of suitable analytical techniques. The amount of noncrystalline and crystalline material in the particles may be determined using standard procedures known in the art, such as by PXRD and DSC analysis. For example, using PXRD analysis, calibration standards may be prepared using samples known to be completely non-crystalline and completely crystalline. Blends of the crystalline and non-crystalline materials are made and the area under the diffraction curve is integrated over an appropriate range of 2θ. A calibration curve of percent crystalline material versus the area under the diffractogram curve is generated from the calibration standards. The crystallinity of the test sample is then determined using these calibration results and the area under the curve for the test sample.

Thus in one embodiment, the particles to be dried comprise a drug, at least one excipient, and residual solvent, wherein a portion of the drug, a portion of the excipient, or a portion of both are in a non-crystalline state. In yet another embodiment, such particles comprise a drug, at least one polymer, and residual solvent, wherein a portion of the drug, a portion of the polymer, or a portion of both are in a non-crystalline state. In still another embodiment, such particles consist essentially of a drug, an excipient (which can be one or more materials), and residual solvent, wherein at least a portion of the drug, a portion of the excipient, or a portion of both are in a non-crystalline state.

The drug-containing particles are formed by a solvent-based process. The terms "solvent-based process" and "solvent process" mean that the process used to form the drug-containing particles makes use of a solvent. Exemplary solvent-based processes include wet granulation, extrusionspheronization, wet milling, spray coating, and spray-drying. In such processes, the drug and excipients may be dissolved in the solvent, suspended in the solvent, wetted by the solvent, or any combination of these. The solvent-based process may involve removal of a portion of the solvent from the particles. In any event, the resulting drug-containing particles contain residual solvent.

Solvents suitable for solvent processing are preferably volatile, with a boiling point of 150° C. or less. In addition, the solvent should have relatively low toxicity and be pharmaceutically acceptable. Preferred solvents include alcohols such as methanol, ethanol, the various isomers of propanol, the various isomers of butanol, 1-pentanol, and 2-methyl-1-propanol; organic acids, such as acetic acid and formic acid; ketones such as acetone, methyl ethyl ketone, methyl isobutyl ketone, cyclohexanone; esters, such as methyl acetate, ethyl formate, ethyl acetate, propyl acetate, and butyl acetate; ethers, such as dimethyl ether, ethyl ether, tert-butyl-methyl ether, 1,2, dimethoxyethane, 2-ethoxyethanol, 2-methoxyethanol, tetrahydrofuran, methyl tetrahydrofuran, 1,3-dioxolane, and 1,4-dioxane; alkanes, such as butane, pentane, hexane, heptane, cyclohexane, and methylcyclohexane; alkenes, such as pentene, hexene, and cyclohexene; nitriles, such as acetonitrile; alkyl halides, such as methylene chloride, chloroform, dichloroethane, dichloroethene, trichloroethane, and trichloroethylene; aromatics, such as benzene, toluene, xylene, ethylbenzene, anisole, cumene, and chlorobenzene; pyridine; and mixtures thereof. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water. Preferred solvents include acetone, methyl ethyl ketone, methyl isobutyl ketone, methanol, ethanol, the various isomers of propanol, methyl acetate, ethyl acetate, toluene, methylene chloride, tetrahydrofuran, 1,4-dioxane, 1,3-dioxolane, and mixtures thereof. Most preferred solvents include acetone, methanol, ethanol, the various isomers of propanol, ethyl acetate, and mixtures thereof. Mixtures of the above with water may also be used.

One solvent-based process suitable for making particles to be dried using the process of the present invention is spray drying. "Spray-drying" is used in its conventional sense and broadly refers to processes involving breaking up liquid mixtures into small droplets (atomization) and rapidly removing solvent from the mixture in an apparatus where there is a strQng driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985), the disclosure of which is incorporated herein by reference.

Various types of nozzles can be used to atomize the spray solution, thereby introducing the spray solution into the spray-dry apparatus as a collection of small droplets. Essentially any type of nozzle may be used to spray the solution as long as the droplets that are formed are sufficiently small that they dry sufficiently (due to evaporation of solvent) that they do not stick to or coat the spray-drying apparatus wall.

Although the maximum droplet size varies widely as a function of the size, shape and flow pattern within the spray-dryer, generally droplets should be less than about 500 μm in diameter when they exit the nozzle. Examples of types of nozzles that may be used to form the particles include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. application Ser. No. 10/351,568, published as U.S. Patent Application No. 2003/0185893A1, the disclosure of which is incorporated herein by reference.

Particles formed in a spray-drying process typically have a mean diameter of less than about 500 μm, more typically less than about 100 μm. For some processes, particles formed by spray drying can have an even smaller mean diameter, such as less than about 50 μm, or even less than about 25 μm in diameter. The particles also typically have low density, having a bulk specific volume of at least about 1.5 mL/g, and more typically at least about 2 mL/g.

In a typical spray-drying process, the final solvent content of the drug-containing particles as they leave the spray-drying chamber is less than about 10 wt %. Since the stability of the pharmaceutical composition as it leaves the spray dryer is typically improved at lower residual solvent concentrations, spray-drying processes may also result in particles containing lower amounts of residual solvent, such as less than about 8 wt %, less than about 6 wt %, less than about 5 wt %, or even less than about 3 wt %. Because it is generally not practical or economical to operate a spray dryer yielding particles having a solvent content of less than about 1 wt %, such particles are preferably dried in the secondary drying process of the invention.

The drug-containing particles may also be formed by spraying the solvent-bearing feed mixture onto seed cores. The seed cores can be made from any suitable material such as starch, microcrystalline cellulose, sugar or wax, by any known method, such as melt- or spray-congealing, extrusion/spheronization, granulation, spray-drying and the like. The feed mixture can be sprayed onto such seed cores using coating equipment known in the pharmaceutical arts, such as pan coaters (e.g., Hi-Coater available from Freund Corp. of Tokyo, Japan, Accela-Cota available from Mariesty of Liverpool, U.K.), fluidized bed coaters (e.g., Würster coaters or top-sprayers available from Glatt Air Technologies of Ramsey, N.J. and from Niro Pharma Systems of Bubendorf, Switzerland) and rotary granulators (e.g., CF-Granulator, available from Freund Corp). During this process, the seed cores are coated with the feed mixture and the solvent is evaporated, resulting in a coating comprising the drug, optional excipients, and residual solvent. The resulting particles are then dried in the secondary drying process of the present invention.

Particles formed by spraying the solvent-bearing feed mixture onto seed cores typically have a mean size after coating of less than about 1000 μm in diameter, and may be less than about 500 μm in diameter, less than about 300 μm in diameter, or even less than about 100 μm in diameter. The particles typically have a bulk specific volume of less than about 5 mL/g, and may be less than about 3 mL/g, or even less than about 2 mL/g.

The Drug

The particles to be dried by the process of the present invention include a drug. The term "drug" is conventional, denoting a compound having beneficial prophylactic and/or therapeutic properties when administered to an animal, especially humans. The process of the present invention is not limited by any class of drugs or any particular drug, but is applicable to a wide range of drugs.

The drug may be in a crystalline, semi-crystalline, amorphous or semi-ordered state or a combination of these states or states that lie between.

The drug may be present in the particles to be dried in an amount ranging from about 1 to about 99 wt %, and most preferably from about 5 to about 80 wt %.

The present invention is particularly suitable for compositions comprising a "low-solubility drug," meaning that the drug has a minimum aqueous solubility at physiologically relevant pHs (i.e., pH 1-8) of about 0.5 mg/mL or less. The drug may have an even lower aqueous solubility, such as less than about 0.1 mg/mL, less than about 0.05 mg/mL, and even less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein (CETP) inhibitors.

Each named drug should be understood to include the neutral form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics Include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, delayerdine, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, levocetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; specific examples of CETP inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester (torcetrapib), [2R,4S]-4-[(3,5-bis-trifluoromethyl-benzyl)-methoxycarbonyl-amino]-2-ethyl-6-trifluoromethyl-3, 4-dihydro-2H-quinoline-1-carboxylic acid ethyl ester, [2R, 4S]-4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2 tetrafluoroethoxy)phenyl]methyl]amino]-1,1,1-trifluoro-2-propanol, (2R,4R,4aS)-4-[amino-(3,5-bis-(trifluoromethyl-phenyl)-methyl]-2-ethyl-6-(trifluoromethyl)-3,4-dihydro-quinoline-1-carboxylic acid isopropyl ester, S-[2-([[1-(2-ethylbutyl)cyclohexyl]carbonyl]amino)phenyl]2-methylpropanethioate, trans-4-[[[2-[[[[3,5-bis(trifluoromethyl)phenyl]methyl](2-methyl-2H-tetrazol-5-yl)amino]methyl]-4-(trifluoromethyl)phenyl]ethylamino] methyl]-cyclohexaneacetic acid, trans-4-[[[2-[[[[3,5-bis(trifluoromethyl)phenyl]methyl](2-methyl-2H-tetrazol-5-yl)amino]methyl]-5-methyl-4-(trifluoromethyl)phenyl]

ethylamino]methyl]-cyclohexaneacetic acid; the drugs disclosed In commonly owned U.S. patent application Ser. Nos. 09/918,127 and 10/066,091, the disclosures of which are incorporated herein by reference; and the drugs disclosed in the following patents and published applications: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; WO 2004020393; EP 992496; and EP 987251, the disclosures of all of which are incorporated by reference.

Solid Amorphous Dispersions

One especially preferred class of drug-containing particles formed by solvent-based processes comprises solid amorphous dispersions of drug and at least one polymer. Suitable polymers for inclusion in solid amorphous dispersions and the other types of solvent-based pharmaceutical composition particles disclosed herein are described infra. At least a major portion of the drug in the dispersion is amorphous, meaning that at least a major portion of the drug in the dispersion is non-crystalline. As used herein, the term "a major portion" of the drug means that at least 60 wt % of the drug in the dispersion is in a non-crystalline form, as opposed to the crystalline form. Thus, the amount of drug in crystalline form does not exceed about 40 wt % of the drug in the dispersion. Preferably, the drug in the dispersion is "substantially amorphous," meaning that the amount of the drug in non-crystalline form is at least 75 wt %. Thus, the amount of drug in crystalline form does not exceed about 25%. More preferably, the drug in the dispersion is "almost completely amorphous," meaning that the amount of drug in non-crystalline form is at least 90 wt %. Thus, the amount of drug in crystalline form does not exceed about 10%.

The amount of drug relative to the amount of polymer present in the solid amorphous dispersions suitable for drying by the process of the present invention depends on the drug and the properties of the polymer and may vary widely from a drug-to-polymer weight ratio of from 0.01 to about 100 (e.g., 1 wt % drug to 99 wt % drug). In most cases it is preferred that the drug-to-polymer ratio is greater than about 0.05 (4.8 wt % drug) and less than about 20 (95 wt % drug).

In one embodiment, the solid amorphous dispersion comprises at least about 5 wt % drug. In another embodiment, the solid amorphous dispersion comprises at least about 10 wt %, at least about 15 wt %, at least about 20 wt %, at least about 25 wt %, at least about 30 wt %, at least about 35 wt %, at least about 40 wt %, or at least about 45 wt % drug.

In another embodiment, the drug and the dispersion polymer constitute at least 60 wt % of the total mass of the solid amorphous dispersion. Preferably the drug and the dispersion polymer constitute at least 70 wt %, more preferably at least 80 wt %, and even more preferably at least 90 wt % of the total mass of the solid amorphous dispersion. In another embodiment the solid amorphous dispersion consists essentially of drug and the dispersion polymer.

The amorphous drug can exist within the solid amorphous dispersion in relatively pure amorphous domains or regions, as a solid solution of compound homogeneously distributed throughout the dispersion polymer or any combination of these states or those states that lie intermediate between them. Preferably, the dispersion is in the form of a "solid solution," meaning that amorphous drug is homogeneously distributed throughout the dispersion polymer, and that the amount of drug present in relatively pure amorphous domains within the solid dispersion is relatively small, on the order of less than 20%, and preferably less than 10% of the total amount of drug. Such solid solutions may also be termed substantially homogeneous.

Solid solutions of drug and a dispersion polymer generally are more physically stable relative to dispersions that are not solid solutions.

Solid amorphous dispersions may be made by a solvent-based process as follows. A feed mixture is formed comprising the drug, a polymer, and a solvent. Preferably, the drug and the polymer are both dissolved in the solvent. The solvent is then rapidly removed from the feed mixture to form particles of drug and polymer. Suitable processes for rapidly removing the solvent include spray-drying, spray-coating, and evaporation. Further details of a suitable spray-drying process for forming solid amorphous dispersions are disclosed in U.S. application Ser. No. 09/131,019 filed Aug. 7, 1998, entitled "Solid Pharmaceutical Dispersions with Enhanced Bioavailability," and published as U.S. Patent Application No. 2002/0009494A1, the disclosure of which is incorporated herein by reference. Following formation, the drug-containing particles are dried in the secondary drying process of the invention.

Adsorbates

Another preferred class of drug-containing particles formed by solvent-based processes is an adsorbate comprising a drug and a substrate. At least a major portion of the drug in the adsorbate is non-crystalline in the same sense noted above in connection with the discussion of solid amorphous dispersions. Preferably, the drug in the adsorbate is substantially non-crystalline, more preferably almost completely non-crystalline and most preferably, the drug is in a completely non-crystalline form within the detection limits of the techniques used for characterization.

The adsorbate includes a high surface area substrate. The substrate is preferably any material that is inert, meaning that the substrate does not adversely interact with the drug to an unacceptably high degree and which is pharmaceutically acceptable. The substrate is also preferably insoluble in the solvent used in the solvent process to form the adsorbate. The substrate should have a high surface area, meaning that its surface area is at least about 20 $m^2$/g, preferably at least about 50 $m^2$/g, more preferably at least about 100 $m^2$/g, and most preferably at least about 180 $m^2$/g. The higher the surface area of the substrate, the higher the drug-to-substrate ratio that can be achieved, which leads to improved physical stability. Thus, effective substrates can have surface areas of from about 200 $m^2$/g, up to about 600 $m^2$/g or more. The substrate should also be in the form of small particles ranging in size of from about 10 nm to about 1 μm, preferably from about 20 nm to about 100 nm. These particles may in turn form agglomerates ranging in size from about 10 nm to about 100 μm.

Solvent processes may be used to form the adsorbates as follows. The drug is first dissolved in a solvent, and then the high surface area substrate is suspended in the solution. The solvent is then rapidly removed from this feed mixture using processes such as spray-drying. Such solvent processes useful in forming the adsorbate particles are described in detail in commonly assigned U.S. patent application Ser. No. 10/173,987, filed Jun. 17, 2002, and published as U.S. Patent Application No. 2003/0054037A1, the disclosure of which is incorporated herein by reference. Following formation, the drug-containing adsorbate particles are dried in the secondary drying process of the invention.

Polymers

In some embodiments, the pharmaceutical composition to be dried may contain a polymer. Polymers suitable for use in the various solvent-processed compositions of the present invention should be pharmaceutically acceptable, and should have at least some solubility in aqueous solution at physiologically relevant pHs (i.e., pH 1-8). Almost any neutral or ionizable polymer that has an aqueous solubility of at least 0.1 mg/mL over at least a portion of the pH 1-8 range is suitable.

In one embodiment the polymer is "amphiphilic" in nature, meaning that the polymer has hydrophobic and hydrophilic portions. It is believed that amphiphilic polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene block copolymers (also referred to as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Maiden, Mass.; amine-functionalized polyacrylates and polymethacrylates; high molecular weight proteins such as gelatin and albumin; and carboxylic acid functionalized starches such as starch glycolate.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

Exemplary non-ionizable cellulosic polymers that may be used as the polymer include: hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, and hydroxyethyl ethyl cellulose.

Exemplary cellulosic polymers that are at least partially ionized at physiologically relevant pHs include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, carboxymethyl ethylcellulose (CMEC), carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate (CAT), methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. Of these cellulosic polymers that are at least partially ionized at physiologically relevant pHs, those that the inventors have found to be most preferred are HPMCAS, HPMCP, CAP, CAT, carboxyethyl cellulose, carboxymethyl cellulose, and CMEC. While specific polymers have been discussed as being suitable for use in the drug-containing particles of the present invention, blends of such polymers may also be suitable. Thus the term "polymer" is intended to include blends of polymers in addition to a single species of polymer.

Of all of the foregoing polymers, those most preferred are HPMCAS, HPMCP, HPMC, CAP, CAT, CMEC, poloxamers, and blends thereof.

Other features and embodiments of the invention will become apparent from the following Examples that are given for illustrating the invention rather than for limiting its intended scope.

DRUGS USED IN EXAMPLES

The following drugs were used in the Examples described below.

Drug 1 was 5-chloro-1H-indole-2-carboxylic acid [(1S)-benzyl-(2R)-hydroxy-3-((3R,4S)-dihydroxy-pyrrolidin-1-yl-)-3-oxypropyl]amide, having the structure

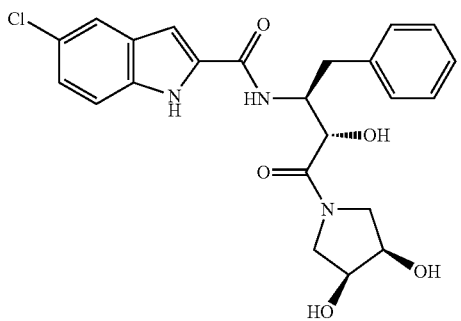 [SMILES: O=C(N[C@@H](Cc1ccccc1)[C@H](O)C(=O)N1C[C@@H](O)[C@@H](O)C1)c1cc2cc(Cl)ccc2[nH]1]

Drug 1 has an aqueous solubility of about 80 μg/mL, and a log P value of about 2.3 as determined by the average value estimated using Crippen's, Viswanadhan's, and Broto's fragmentation methods. The $T_m$ of crystalline Drug 1 was determined by DSC analysis to be 238° C., while the $T_g$ of amorphous Drug 1 was determined by DSC analysis to be 96° C.

Drug 2 was torcetrapib having the structure

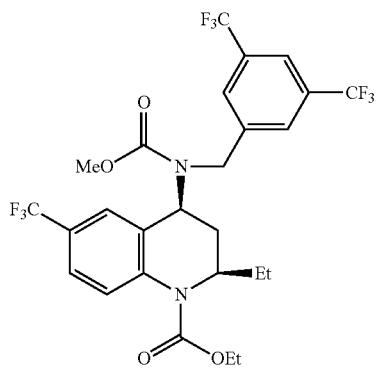 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

Drug 2 has an aqueous solubility of less than 0.1 μg/mL, and a Log P value of 7.0, as determined by the average value estimated using Crippen's, Viswanadhan's, and Broto's fragmentation methods. The $T_m$ of crystalline Drug 2 was determined by DSC analysis to be 95° C., while the $T_g$ of amorphous Drug 2 was determined by DSC analysis to be 29° C.

Drug 3 was (4R)—N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, having the structure

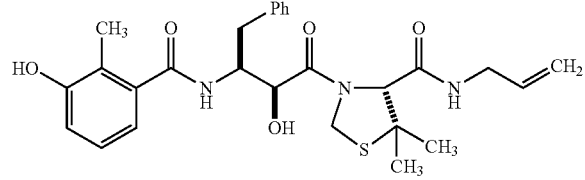

Drug 3 has an aqueous solubility of about 1600 μg/mL, and a Log P value of 4.6, as determined by the average value estimated using Crippen's, Viswanadhan's, and Broto's fragmentation methods. The $T_m$ of crystalline Drug 3 was determined by DSC analysis to be 178° C., while the $T_g$ of amorphous Drug 3 was determined by DSC analysis to be 99° C.

Dispersion 1

A solid amorphous dispersion comprising 50 wt % of Drug 1 and 50 wt % HPMCAS was formed as follows. First, a spray solution was formed containing 10.0 g Drug 1, 10.0 g HPMCAS-MG, 9.0 g water, and 171.0 g acetone. The spray solution was pressurized and fed to a spray drier through a pressure nozzle (Schlick 2; Dusen Schlick, GmbH of Untersiemau, Germany), at a flow rate of about 37 g/min. The drying gas entered the spray-drying chamber at a flow of about 350 g/min, with an inlet temperature of about 120° C. The spray-dried particles, evaporated solvent, and drying gas exited the spray-drying chamber at a temperature of 46° C., and the spray-dried particles were collected in a cyclone separator.

Four 10-mg samples of Dispersion 1 were placed onto sample pans. The sample pans were placed in an environmental chamber at ambient temperatures and controlled humidity (0% RH, 25% RH, 50% RH and 75% RH) and equilibrated for about 14 hours, after which they were crimped and sealed. Following equilibration, the samples were loaded into a Thermal Analysis Q1000 Differential Scanning Calorimeter (DSC) equipped with an autosampler. The samples were heated by modulating the temperature at ±1.5° C./min, and ramping at 2.5° C./min to 220° C. Glass transition temperatures were determined from the DSC scans. The results are plotted in FIG. 3, and clearly show decreasing $T_g$ of the dispersion with increasing relative humidity.

Dispersion 2

A solid amorphous dispersion comprising 25 wt % of the drug torcetrapib (Drug 2) and 75 wt % HPMCAS-MG was formed in a manner similar to procedures described for Dispersion 1.

Dispersion 3

A solid amorphous dispersion comprising 90 wt % Drug 3 and 10 wt % HPMCAS was prepared using the procedure described for Dispersion 1 except that the spray solution contained 18.08 g Drug 3, 2.007 g HPMCAS (AQOAT-MG from Shin Etsu), and 180 g acetone, and the spray solution was delivered to the pressure nozzle at a flow rate of about 28 g/min.

Dispersion 4

A solid amorphous dispersion comprising 90 wt % Drug 3 and HPMCAS was prepared as follows. First, a spray solution was formed containing 3319.1 g Drug 3, 368.8 g HPMCAS-MG, and 14.76 kg methanol. The spray solution was pumped using a high-pressure pump to a spray drier (a Niro type XP Portable Spray-Drier with a Liquid-Feed Process Vessel ("PSD-1")), equipped with a pressure nozzle (Schlick 3). The spray solution was pumped to the spray drier at about 85 g/min. Drying gas (1800 g/min nitrogen) was circulated through a diffuser plate at an inlet temperature of 125° C. The evaporated solvent and drying gas exited the spray drier at a temperature of 56° C. The resulting solid amorphous dispersion was collected in a cyclone.

Example 1

Figure 3:
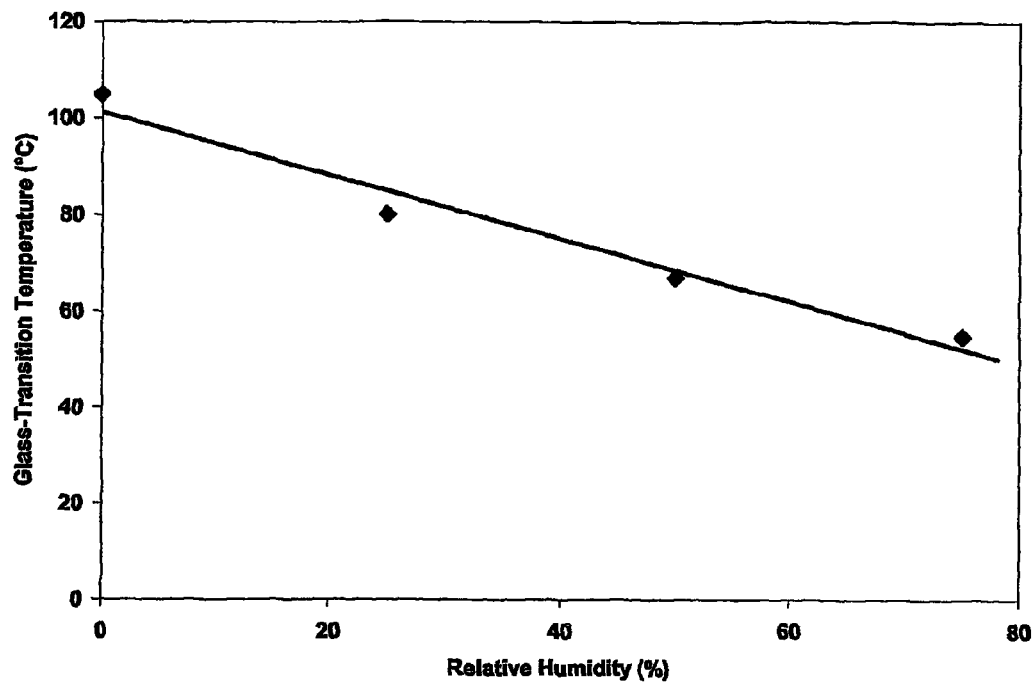
FIG. 3 is a graph showing the relationship between the glass transition temperature of a pharmaceutical composition made by a solvent-based process and relative humidity in the drying environment.

Dispersion 1 was dried using the process of the present invention using water vapor as the volatile mobility-enhancing agent according to the following procedure. A Gruenberg single-pass convection tray drier was equipped with a commercial humidifier connected to the incoming stripping gas system. The temperature of the drying chamber was maintained at 40° C., while the relative humidity was set at 75%; thus, the partial pressure of water vapor in the drying chamber was about 0.055 atm. As shown in FIG. 3, the Tg of control particles that are free from the volatile mobility-enhancing agent and the residual solvent is about 105° C., whereas the Tg of particles of Dispersion 1 exposed to a relative humidity of 75% was about 55° C.

As a control (Control 1), the same dispersion was placed in a Gruenberg single-pass convection tray drier, with the temperature maintained at 40° C., and the relative humidity maintained at 10%; thus, the partial pressure of water vapor in the drying chamber was about 0.007 atm.

Samples of the spray-dried dispersions were removed from the drying chamber during each drying operation and analyzed for residual solvent content by headspace gas chromatography (GC). Specifically, dispersion samples were initially collected at 2 minutes, then at 10-minute intervals during the first hour of drying, then at 90, 120, 180 and 240 minutes if necessary. For the GC analysis, a sufficient amount of the dispersion was taken at each time interval to fill a vial completely, with minimal void space. The vial was then sealed and stored at 0° C. until analysis. To analyze each sample, the sample was weighed, and dimethyl acetamide (DMAC) was added to dissolve the sample. Each sample in DMAC was injected onto a GC column and the solvent peak area was compared to standards to determine the amount of solvent in the dispersion sample. The weight of residual solvent as a percentage of the total sample weight was calculated.

Figure 4:
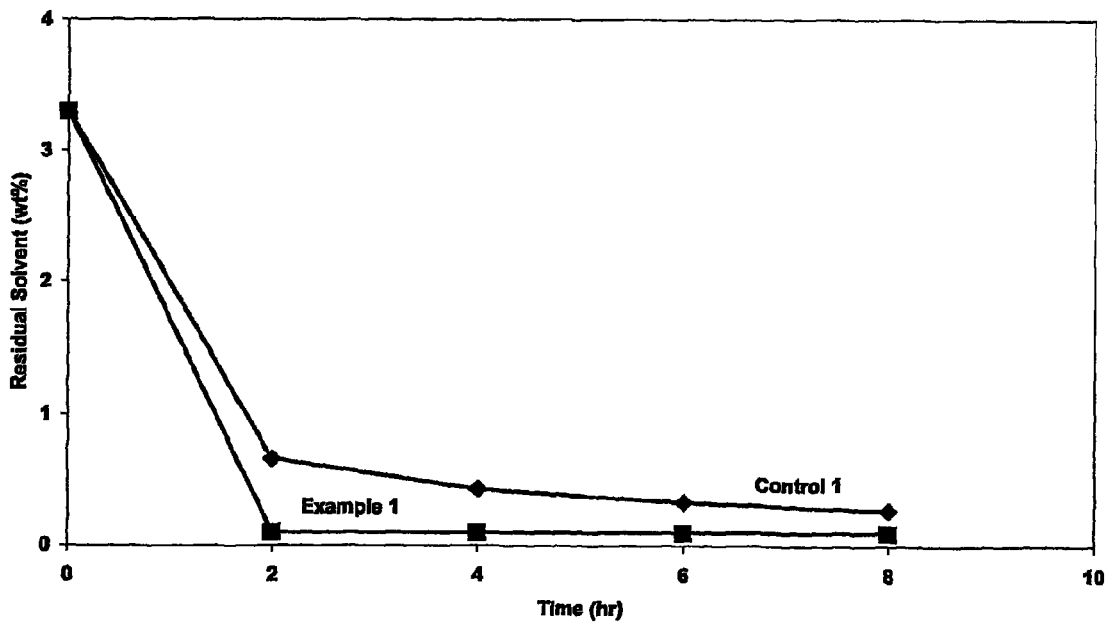
FIGS. 4-7 are graphs showing residual solvent content in relation to time for various pharmaceutical compositions dried using the process of the present invention.

The results of these tests are shown in FIG. 4 and show that the concentration of residual acetone in the dispersion dried under humidified conditions (Example 1, 75% RH) decreased at a faster rate than the sample dried under dry conditions (Control 1, 10% RH). Indeed, the concentration of residual acetone in the dispersion of Example 1 was less than 0.1 wt % after less than 2 hours of drying, while the concentration of residual acetone in the Control sample was 0.27 wt % after 8 hours of drying at 10% RH.

Example 2

Figure 5:
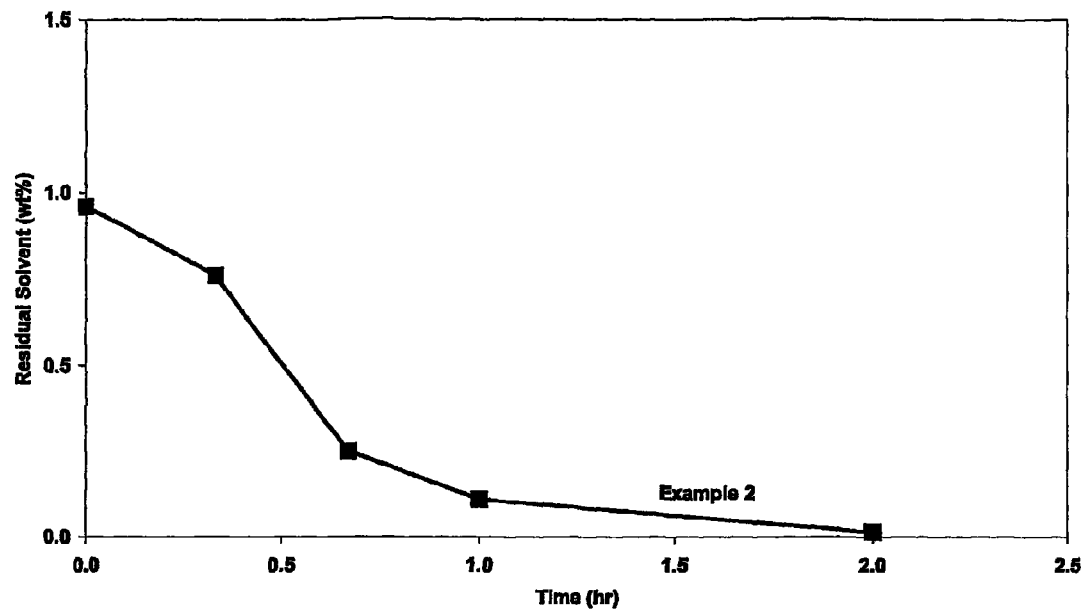

A secondary drying apparatus of substantially the configuration shown in FIG. 1 was fabricated by modifying a VPT vertical process drier from Ekato (Schopfheim, Germany) with a 3-liter capacity and an agitator diameter of 0.2 m by fitting it with dual gas inlets near the head space of the drying chamber so that a humidified stripping gas of nitrogen could be fed into the drying chamber. A flash humidification system similar to a commercial humidifier was fabricated to fit the modified Ekato drier with a throttle control valve to introduce precise amounts of water so as to control the relative humidity at 70% RH. The vacuum pump was protected from condensation using a condenser. The agitator mixing speed was 125 rpm, the humidified stripping gas flow rate was 1.0 standard liters/min, and the chamber pressure was maintained at 120 mbar. Hot water was circulated through the jacketed drying chamber to maintain the temperature at 50° C. Thus, the partial pressure of water vapor in the drying chamber was about 0.086 atm For Example 2, the drying chamber was charged with 600 g (about 2 liters) of Dispersion 2. Samples of the dried dispersion were analyzed for residual solvent using the procedures outlined in Example 1. The results are shown in FIG. 5, and show that the concentration of residual solvent in the dispersion decreased to less than 0.1 wt % acetone in less than 2 hours.

Example 3

Figure 6:
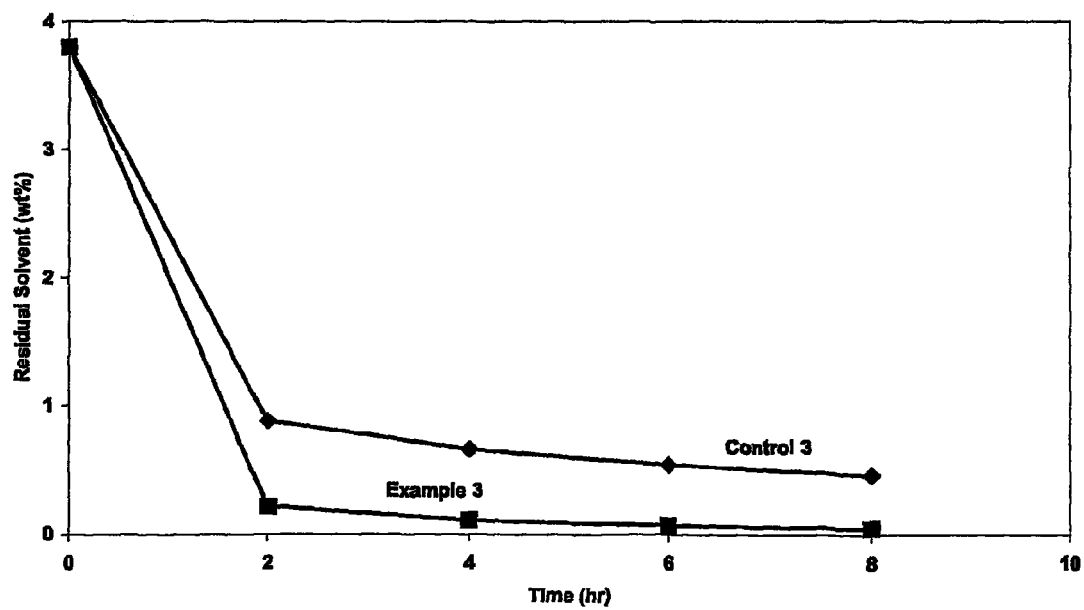

Dispersion 3 was dried using the process of the present invention following the procedure outlined for Example 1. As a control (Control 3), a sample of Dispersion 3 was dried at 40° C. and 10% RH. Samples were analyzed for residual solvent using the procedures outlined in Example 1. The results are shown in FIG. 6, and shown that the concentration of residual acetone decreased much more rapidly when the dispersion was dried at 75% RH than at 10% RH.

Example 4

Figure 7:
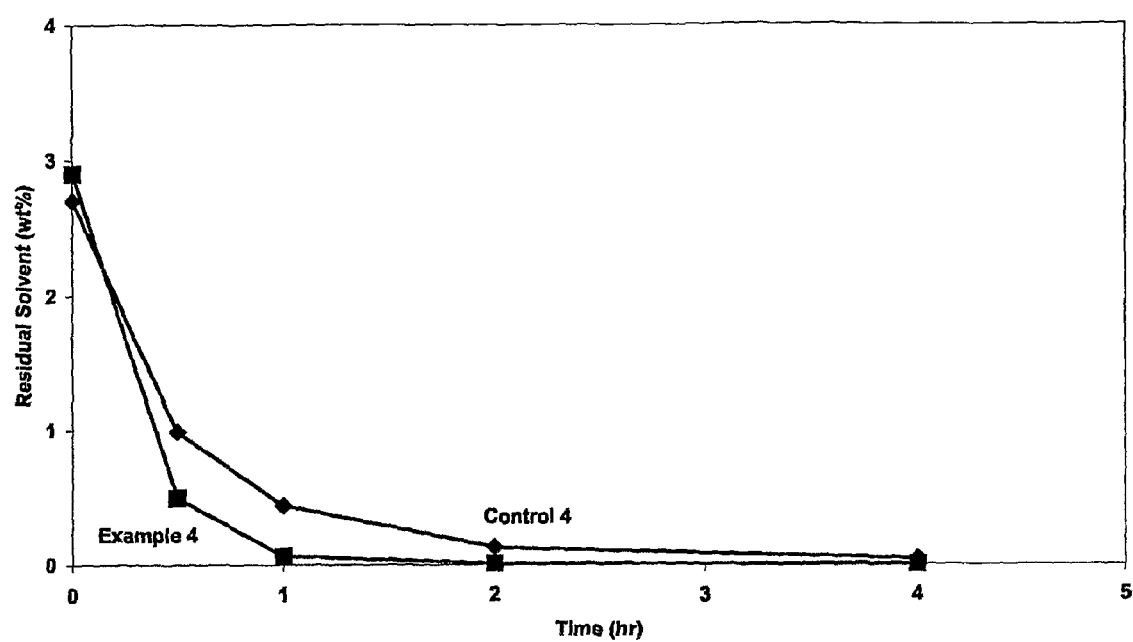

Dispersion 4 was dried using the procedure outlined for Example 2. As a control (Control 4), a sample of Dispersion 4 was dried using the procedure outlined for Example 2, except that the relative humidity in the drying chamber was maintained at 10% RH. Samples of the dispersions were periodically removed and analyzed for residual analysis using the procedures outlined for Example 1. The results of these tests are shown in FIG. 7, and show that the concentration of residual methanol decreased much more rapidly when the dispersion was dried at 75% RH than at 10% RH.

In Vitro Dissolution Test

A sample of Dispersion 4 was evaluated before and after secondary drying in an in vitro dissolution test to determine the effect of drying on concentration enhancement. For this test, a sufficient amount of Dispersion 4 was added to microcentrifuge test tubes so that the concentration of Drug 3 would have been 3000 µg/mL had all of the drug had dissolved. The test was performed in duplicate. The tubes were placed in a 37° C. temperature-controlled chamber, and 1.8 mL PBS at pH 6.5 and 290 mOsm/kg was added to each tube. The samples were mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high performance liquid chromatography (HPLC). The contents of each tube were mixed on the vortex mixer and allowed to stand undisturbed at 37° C. until the next sample was taken. Samples were collected at 4, 10, 20, 40, 90, and 1200 minutes. For comparison, crystalline Drug 3 alone was tested using the same procedures.

The concentrations of drug obtained in these samples were used to determine the maximum concentration of drug ($MDC_{90}$) and the area under the concentration-versus-time curve ($AUC_{90}$) during the initial 90 minutes. The results are shown in Table 1.

TABLE 1

| Sample | $MDC_{90}$ (µg/mL) | $AUC_{90}$ (min*µg/mL) |
|---|---|---|
| Dispersion 4 (before secondary drying) | 1235 | 107,100 |
| Dispersion 4 (after secondary drying) | 1318 | 111,900 |
| Crystalline Drug 3 | 112 | 9200 |

The results in Table 1 show that the $MDC_{90}$ and $AUC_{90}$ of Dispersion 4 are about the same before and after secondary drying. Dispersion 4 before secondary drying provided an $MDC_{90}$ that was 11.0-fold that provided by crystalline drug, and an $AUC_{90}$ that was 11.6-fold that provided by crystalline drug. After secondary drying, Dispersion 4 provided an $MDC_{90}$ that was 11.8-fold that provided by crystalline drug, and an $AUC_{90}$ that was 12.2-fold that provided by crystalline drug.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:
1. A process for producing pharmaceutical composition comprising:
  (a) spraying a mixture comprising a drug, an excipient and a solvent and performing a first solvent removing step to form at least partially non-crystalline, dry drug-containing particles, wherein said dry drug-containing particles contain less than about 10 wt % of said solvent; and (b) performing a second solvent removing step by
  (i) introducing said dry particles into a chamber;
  (ii) introducing into said chamber a volatile mobility-enhancing agent that is different from said solvent;
  (iii) introducing a stripping gas into said chamber;
  (iv) exposing said dry particles in said chamber to said mobility-enhancing agent and said stripping gas; and
  (v) removing said stripping gas and said mobility-enhancing agent from said chamber along with at least a portion of said solvent wherein the amount of mobility-enhancing agent present in said chamber is such that during the second solvent removing step said dry particles have a glass transition temperature that is less than the glass transition temperature of such particles free of said solvent and said mobility-enhancing agent, but greater than the temperature at which said second solvent removing step is performed and wherein the amount of solvent remaining in said particles after performing the second solvent removing step is less than about 0.5 wt % of the total mass of said particles.

2. The process of claim 1 wherein said glass-transition temperature of said particles is reduced by at least 5° C. relative such particles free of said solvent and said volatile mobility-enhancing agent.

3. The process of claim 1 wherein said volatile mobility-enhancing agent is selected from the group consisting of water, ethanol, isopropyl alcohol, carbon dioxide, and mixtures thereof.

4. The process claim 3 wherein said volatile mobility-enhancing agent is present in said chamber at a partial pressure of at least 0.02 atm.

5. The process of claim 3 wherein said volatile mobility-enhancing agent is water and wherein the relative humidity in said chamber is at least about 30%.

6. The process of claim 1 wherein said stripping gas is the same as said volatile mobility-enhancing agent.

7. The process of claim 1 wherein said chamber is heated to a temperature of from about 25° C. to about 100° C.

8. The process of claim 1 wherein the pressure in said chamber is less than about 0.75 atm.

9. The process of claim 1 wherein said excipient is a polymer.

10. The process of claim 9 wherein said particles are in the form of a solid amorphous dispersion of said drug in said polymer.

11. The process of claim 1 wherein said drug is selected from the group consisting of antihypertensives, antianxiety agents, anticlotting agents, anticonvulsants, blood glucose-lowering agents, decongestants, antihistamines, antitussives, antineoplastics, beta blockers, antiinflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial agents, antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

* * * * *